United States Patent [19]

Ratledge

[11] 3,997,322
[45] Dec. 14, 1976

[54] HERBICIDE CARRIER OIL COMPOSITION

[75] Inventor: Edward L. Ratledge, Claymont Heights, Del.

[73] Assignee: Sun Oil Company of Pennsylvania, Philadelphia, Pa.

[22] Filed: Sept. 9, 1970

[21] Appl. No.: 70,876

[52] U.S. Cl. .................................... 71/93; 71/88; 71/113; 71/117; 71/DIG. 1
[51] Int. Cl.$^2$ ............................................ A01N 9/22
[58] Field of Search ........................ 71/93, DIG. 1

[56] References Cited

UNITED STATES PATENTS

| | | | |
|---|---|---|---|
| 2,891,855 | 6/1959 | Gysin et al. | 71/93 |
| 2,957,803 | 10/1960 | Woods | 71/DIG. 1 |
| 3,172,816 | 3/1965 | Swintosky | 71/79 X |
| 3,551,134 | 12/1970 | Brenteson | 71/118 |
| 3,709,676 | 1/1973 | Vantiak | 71/92 |

FOREIGN PATENTS OR APPLICATIONS

| | | | |
|---|---|---|---|
| 803,772 | 10/1958 | United Kingdom | 71/DIG. 1 |

*Primary Examiner*—Glennon H. Hollrah
*Attorney, Agent, or Firm*—J. Edward Hess; Donald R. Johnson; Anthony Potts, Jr.

[57] ABSTRACT

An agricultural spray oil composition comprising a major amount of a petroleum hydrocarbon oil having an unsulfonated residue of at least 75 and a viscosity at 100° F. in the range of 60 to 350, and a minor amount of a vegetable oil. The spray oil composition provides a particularly improved carrier which enhances the effectiveness of selective herbicides.

2 Claims, No Drawings

HERBICIDE CARRIER OIL COMPOSITION

BACKGROUND OF THE INVENTION

Annual grasses and large broadleafed weeds have hindered the growing of corn, sugar beets, sorghum, sugar cane, macadamia orchards and pineapples. Cultivation of crops, which heretofore was the most widely used method of eliminating weeds, has given way more recently to the use of pre-emergence and postemergence selective herbicides.

Pre-emergence selective herbicides are applied directly to the soil during or just prior to the planting season. Postemergence selective herbicides are applied to the fields after the weeds have begun to grow and preferably before they have reached the height of six inches or more. Weeds which most seriously plague farmers include lambsquarters (*Chenopodium album*), ragweed (*Ambrosia artemisiifolia*), barnyard grass (*Echinochloa crusgalli*), smartweed (*Polygonum pennsylvanicum*), velvet leaf (*Abutilon theophrasti*), quackgrass (*Agropyron repens*), witchgrass (*Panicum capillare*), redroot pigweed (*Amoranthus retroflexus*), yellow foxtail (*Setaria glauca*), giant foxtail (*Setaria faberi*), large crabgrass (*Digitaria sanguinalis*), fall panicum (*Panicum dichotomiflorum*), yellow nutsedge (*Cyperus esculentus*) and others.

Many of these weeds present a real problem to farmers because they often reinvade the fields in midsummer usually after pre-emergence herbicides are no longer effective. Postemergence herbicides are now normally required to sustain production of crops when the midsummer invasion of weeds occur.

Compounds such as substituted diamino, chloro triazines, chlorinated organic acids and their salts and esters, as well as many organo, phosphor and sulfur compounds have been demonstrated to be effective postemergence selective herbicides for combating undesired plant growth of the species of weeds hereinabove disclosed.

Of these herbicides one of the most widely used is the substituted diamino,chloro-S-triazines. This class of compounds can be generally defined by the structural formula

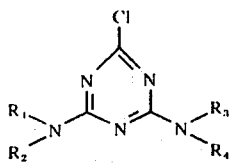

wherein $R_1$ $R_2$ $R_3$ and $R_4$ can each be selected from the group consisting of the hydrogen and alkyl, cycloalkyl alkenyl, hydroxyalkyl, arathyl radicals. Compounds of the type herein defined are disclosed in U.S. Pat. No. 2,891,855 issued June 23, 1959. Some of the compounds defined include:

2-chloro-4-ethylamino-6-isopropylamino-5-triazine
2-chloro-4-amino-6-ethylamino-5-triazine
2-chloro-4-amino-6-n-propylamino-5-triazine
2-chloro-4-amino-6-n-butylamino-5-triazine
2-chloro-4-amino-6-alkylamino-5-triazine
2-chloro-4-amino-6-diethylamino-5-triazine
2-chloro-4-methylamino-6-ethylamino-5-triazine
2-chloro-4-methylamino-6-n-propylamino-5-triazine
2-chloro-4,6-bis-ethylamino-5-triazine
2-chloro-4-ethylamino-6-propylamino-5-triazine
2-chloro-4-ethylamino-6-($\beta$-hydroxy-ethylamino)-5-triazine
2-chloro-4-ethylamino-6-diethylamino-5-triazine
2-chloro-4,6-bis-diethylamino-5-triazine and others. Herbicidal compounds such as 2,4-dichloropropionic acid and 2,4-dichlorophenoxyacetic acid are also included among the postemergence organic herbicides known to the art. Many of these well known selective herbicides are also disclosed in "Herbicide Handbook of the Weed Society of America," First Ed. 1967, W. F. Humphrey Press Inc., Geneva, N.Y.

Recently it has been disclosed that petroleum hydrocarbon spray oils in aqueous emulsion form provide carriers which enhance the effectiveness of certain herbicides. It has also been disclosed that certain emulsifying agents as well as vegetable oil or crop oil emulsions also effectively enhance the weed killing function of the herbicide when combined with these carriers. For example, it was reported by John D. Naleweja in an abstract published in "Proceedings North Central Weed Control Conference", (December, 1968, Indianapolis, Ind.), page 12 that sunflower oil-in-water emulsions and linseed oil-in-water emulsions were as effective as petroleum hydrocarbon oil-in-water emulsions when used as carriers for 2-chloro-4-ethylamino-6-isopropylamino-S-triazine (atrazine) when used as a postemergence herbicide. The paper discloses that 1 gallon per acre of crop seed oil was as effective as 1 gallon per acre of petroleum hydrocarbon oil as a carrier for atrazine herbicide in combating weed growth. A new herbicide carrier oil composition which substantially enhances the effectiveness of herbicides while requiring much less oil has now been discovered.

DESCRIPTION OF THE INVENTION

It has now been discovered that a spray oil composition comprising a major amount of petroleum hydrocarbon agricultural spray oil and a minor amount of vegetable oil provides an emulsifiable oil composition particularly effective as a carrier for selective herbicides. It has been discovered that a composition comprising 1 part up to 9 parts spray oil per 1 part of vegetable provides an agricultural spray oil composition which as a concentrate or in the diluted aqueous emulsion form provides an effective carrier composition which substantially enhances the herbicidal activity of selective herbicides.

The petroleum hydrocarbon oil component of the compositions of the present invention is preferably a solvent refined fraction of petroleum oil composed primarily of paraffinic and naphthenic hydrocarbons containing less than 25 wt. percent aromatics. The oils as herein described are usually referred to as agricultural crop spray oils. Petroleum hydrocarbon oil fractions classified in this category can be generally defined as follows:

| | |
|---|---|
| Gravity, ° API/60° F. | 31.0–36.0 |
| Viscosity, SUS/100° F. | 60–120 |
| Viscosity, SUS/210° F. | 34–38 |
| Flash point, ° F. | 300–400 |
| Fire point, ° F. | 375–400 |
| Pour temperature, ° F. | −10 to +20 |
| Unsulfonated residue, wt. percent (ASTM) | 75.0–99.9 |
| Refractive index, 25° C. | 1.4660–1.4690 |
| Gel aromatics, wt. percent, max. | 25.0 |
| Distillation range at 10 mm. Hg | |

| (ASTM D-1160) | 300–500 |
|---|---|

The second component of the compositions of the present invention is a vegetable seed oil or a mixture of vegetable seed oils, as they are known in the agricultural industry, crop seed oils which are produced from the particular crop from which their name is derived. Included in the vegetable oils suitable for the compositions of the present invention are cotton seed oil, rapeseed, peanut oil, sunflower oil, linseed oil, safflower oil, soybean oil, corn oil, olive oil and blends of the above oils such as cotton seed oil plus soybean oil; cotton seed oil plus peanut oil; cotton seed oil plus olive oil; corn oil plus linseed oil; corn oil plus soybean oil; as well as blends of any two or more of the above disclosed vegetable oils.

Petroleum hydrocarbon agricultural spray oil and the vegetable oils of the compositions of the present invention are normally blended in the ratio of 1 part up to 9 parts of petroleum hydrocarbon oil to 1 part of vegetable oil. The preferred ratio of petroleum hydrocarbon oils to vegetable oils is 1 to 7 parts petroleum hydrocarbon oil to 1 part vegetable oil. The blended oils are normally prepared as emulsifiable compositions by adding from 0.1 to 10 parts and preferably 1 to 3 parts emulsifier per 100 parts of the combined blended oils.

The blended petroleum hydrocarbon oil and vegetable oil composition plus the emulsifying quantity of the emulsifying agent can be thereafter diluted with 20 to 160 gallons of water to 1 quart of the oil composition for application to crop fields. Normally, when used as herbicide carrier, the quantity of herbicide is added prior to the dilution with water of the concentrated oil-emulsifying agent mixture. The normal application rate of the diluted emulsion plus herbicide is 5 to 40 gallons of diluted spray oil herbicide composition per one acre of crop. The herbicide is normally added in the quantity of 0.5 to 3 pounds of herbicide per acre of crop to be treated in accordance with the particular requirements and characteristics of the herbicide to be used.

The emulsifying agents particularly suited for use in the compositions of the present invention are ionic or nonionic surface active compounds generally well known to the art. Surface active agents are suitable as a class for use according to the present invention. The nature of surface activations is well known and such agents generally have an oleophilic portion of the molecule, usually of hydrocarbon nature, and another, polar portion of the molecule, which may be provided by various functional groups such as hydroxyl, sulfate, carboxyl, carbonyl, amino, nitro, amide, ether, sulfonate, phosphate, phosphite, etc. Examples of suitable classes of surface active agents which can be employed are alkali metal salts of fatty acids, alkali metal salts of sulfated fatty acids, fatty acid glycerides, sulfonated or sulfated fatty acid esters or amides, alkali metal sulfates, alkali metal alkyl sulfonates, alkali metal aryl sulfonates, alkali metal alkyl lauryl sulfonates, quaternary ammonium halides, alkali metal salts of alkylated naphthalene, sulfonic acid, polyethylene sorbitol esters of fatty acids, fatty acid amides of alkanol amines, condensation products of ethylene oxide and polyalkylene glycols, sorbitan esters, alkyl substituted phosphoric acids, alkali metal salts of alkyl phenol sulfonates, etc. Examples of individual surface active agents which can be employed are given for example in Kirk et al., ENCYCLOPEDIA OF CHEMICAL TECHNOLOGY, Volume 13, pages 515–517 (1954).

Particularly suitable surface active agents for use according to the invention are polyalkyl amine and fatty amides of which numerous examples are given in the Kirk et al. disclosure referred to in the preceding paragraph.

The compositions of the present invention are normally prepared as oil herbicide concentrates containing an emulsifying agent. The herbicide is added to the oil concentrate and the mixture is thereafter diluted to the desired volume of composition with water. Normally, the required application of oil plus herbicide per acre of crop is determined in accordance with the area to be treated. The herbicides suitable for use with the hereinabove disclosed compositions are selective herbicides as a class and in particular those herbicides which have been disclosed above.

Particularly suited for use in combination with the carrier compositions of the present invention are the chloro-amino-S-triazine compounds. Of this group of herbicides, the most frequently used compound is 2-chloro-4-ethylamino-6-isopropylamino-1,3,5-triazine, more generally known as atrazine. Also, herbicides such as 2,2-dichlorophenoxy acetic acid are among those herbicide compositions which are in widespread use and which are particularly suitable for use with the carriers of the present invention.

A particular advantage of the use of the carrier compositions of the present invention is that substantially less of the carrier oil is required to accomplish the same results in weedkill as can be accomplished with the other well known oil carriers. For example, normally it is required to use 2 pounds of atrazine per 1 gallon of petroleum hydrocarbon spray oil in order to substantially reduce weed growth in a corn field of one-acre size. Also, when vegetable oils are used, it is known that it normally requires 1 quart of vegetable oil and 2 pounds of atrazine in order to accomplish substantially equal herbicidal effects in the same corn field under the same conditions. However, use of the oil compositions of the present invention, i.e., 1 quart of the combined petroleum hydrocarbon oil and vegetable oil, is equally effective as 1 gallon of the petroleum hydrocarbon oil alone or 1 quart of the vegetable oil alone thereby providing substantial economic advantage to the user of this carrier composition. To illustrate this point, the following examples are given:

EXAMPLE I

A spray oil composition was prepared by adding 3 ounces of liquid emulsifying agent to 1 gallon of a petroleum hydrocarbon oil characterized as having a viscosity at 100° F. of 115, API Gravity at 33.5, a distillation range at 10 millimeters mercury between 300°–500° F., an unsulfonated residue of 92 and thereafter diluting the emulsion in oil with 40 gallons of water. To this solution was added 2 pounds of 2-chloro-4-ethylamino-6-isopropylamino-S-triazine (atrazine).

EXAMPLE II

A spray oil composition was prepared by blending 1½ pints of the petroleum hydrocarbon oil of Example I with ½ pint of cotton seed oil and 3 ounces of liquid emulsifying agent. The blend was thereafter diluted with 40 gallons of water to which was added 2 pounds of atrazine.

EXAMPLE III

A composition was prepared in the identical manner as disclosed in Example II with the exception that rapeseed oil was substituted for cotton seed oil.

EXAMPLE IV

A herbicidal composition was prepared in the identical manner as disclosed in Example II with the exception that peanut oil was substituted for cotton seed oil.

EXAMPLE V

A herbicidal composition identical to that of Example II was prepared with the exception that sunflower seed oil was substituted for cotton seed oil.

EXAMPLE VI

A herbicidal spray oil composition was prepared in an identical manner as that disclosed in Example II with the exception that linseed oil was substituted for cotton seed oil.

EXAMPLE VII

A herbicidal composition identical to that of Example II was prepared with the exception that sunflower oil was substituted for cotton seed oil.

EXAMPLE VIII

A herbicidal composition identical to that of Example II was prepared with the exception that soybean oil was substituted for cotton seed oil.

EXAMPLE IX

A herbicidal composition identical to that of Example II was prepared with the exception that corn oil was substituted for cotton seed oil.

EXAMPLE X

A herbicidal composition identical to that of Example II was prepared with the exception that olive oil was substituted for cotton seed oil.

EXAMPLE XI

A herbicidal composition identical to that of Example II was prepared with the exception that a blend of 50 parts cotton seed and 50 parts soybean oil was substituted for the cotton seed oil.

EXAMPLE XII

A herbicidal composition identical to that of Example II was prepared with the exception that a blend of 50 parts peanut oil and 50 parts corn oil was substituted for the cotton seed oil.

EXAMPLE XIII

Two pounds of atrazine was emulsified with 3 ounces of emulsifying agent in 40 gallons of water. This example is to serve as control.

Each of the compositions of the thirteen examples disclosed above were applied at the rate of 40 gallons per acre to corn fields approximately 1 month after planting. Evaluations for weed growth were made approximately 2 weeks after this spraying was completed. The treatments were evaluated for grass and broadleafed weed control and corn injury. The spectrum of weed species found growing in the corn fields at the time of evaluation included lambsquarter, ragweed, barnyard grass, smartweed, velvet leaf, quack grass and witchgrass. Corn injury was not observed in any of the fields where the combination herbicidal spray oils and herbicides were applied. A review of the data of the effectiveness of herbicide compositions as shown in the table below clearly illustrates that the combination of vegetable oils as hereinabove disclosed with petroleum hydrocarbon spray oils provides a carrier composition for application of atrazine to growing weeds which substantially enhances the effectiveness of the atrazine in combating those growing weeds. As hereinbelow shown 1 quart of the vegetable oil petroleum hydrocarbon oil combination as carrier for the atrazine herbicide provided a herbicidal composition which was more effective than the combination of atrazine and 1 gallon of the hydrocarbon spray oil. By the data in the table hereinbelow presented, the economic advantages of the application of herbicides particularly atrazine to weeds using the petroleum hydrocarbon oil-vegetable oil composition carrier is clearly illustrated.

TABLE I

| Example No. | Herbicide | Carrier ¾ Petroleum Oil Plus | Weed Control Bd Leaf | Grasses | Corn Injury |
|---|---|---|---|---|---|
| I | Atrazine | 7¼ qt. Petroleum Oil | 9.8 | 8.5 | 0.0 |
| II | Atrazine | ¼ qt. Cotton Seed Oil | 9.8 | 9.0 | 0.0 |
| III | Atrazine | ¼ qt. Rapeseed Oil | 9.7 | 9.0 | 0.1 |
| IV | Atrazine | ¼ qt. Peanut Oil | 8.9 | 8.0 | 0.0 |
| V | Atrazine | ¼ qt. Sunflower Seed Oil | 9.0 | 8.5 | 0.0 |
| VI | Atrazine | ¼ qt. Linseed Oil | 9.5 | 8.5 | 0.0 |
| VII | Atrazine | ¼ qt. Safflower Oil | 9.8 | 9.0 | 0.0 |
| VIII | Atrazine | ¼ qt. Soybean Oil | 8.8 | 7.0 | 0.0 |
| IX | Atrazine | ¼ qt. Corn Oil | 9.0 | 8.5 | 0.0 |
| X | Atrazine | ⅛ qt. Safflower Oil | 9.5 | 9.0 | 0.0 |
| XI | Atrazine | ⅛ qt. Cotton Seed Oil | 9.5 | 9.0 | 0.0 |
| | | ⅛ qt. Soybean Oil | 8.5 | 7.5 | 0.0 |
| XII | Atrazine | ⅛ qt. Peanut Oil | 8.5 | 8.0 | 0.0 |
| | | ⅛ qt. Corn Oil | 9.5 | 9.0 | 0.0 |

TABLE I-continued

| Example No. | Herbicide | Carrier ¾ Petroleum Oil Plus | Weed Control Bd Leaf | Grasses | Corn Injury |
|---|---|---|---|---|---|
| XIII | Atrazine | None | 8.5 | 6.5 | 0.0 |

The compositions of the present invention include selective herbicides as a class and particularly applicable where mixtures of different herbicidal compounds are applied. For example, mixtures of atrazine and 2,2-dichloropropionic acid and mixtures of atrazine and 2,4-dichlorophenoxyacetic acid can be applied in the manner disclosed in the examples above with substantially identical results being obtained.

The invention claimed is:

1. An improved postemergence herbicidal spray oil composition particularly effective in selectively controlling unwanted plant growth consisting essentially of:
   (a) 1 to 9 parts of a petroleum hydrocarbon oil characterized as having an unsulfonated residue of at least 75 and a viscosity at 100° F. in the range of 60 to 350;
   (b) 1 part of a vegetable oil selected from the group consisting of cottonseed oil, rapeseed oil, peanut oil, sunflower oil, linseed oil, soybean oil, corn oil, olive oil and mixtures thereof;
   (c) an emulsifying agent and
   (d) a herbicidally effective quantity of a compound of the formula

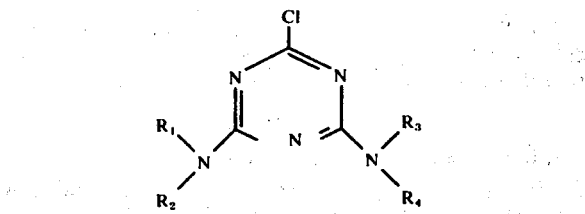

wherein $R_1$ $R_2$ $R_3$ and $R_4$ represent a member selected from the group consisting of hydrogen, alkyl, alkenyl, hydroxyalkyl, arakyl and cycloalkyl radicals and each of the pairs of radicals $R_1$ and $R_2$ and $R_3$ and $R_4$ together with the corresponding nitrogen atom represents a member selected from the group consisting of five or six membered alkylamino radicals and the morpholino radical.

2. A composition according to claim 1 wherein the petroleum hydrocarbon oil is characterized as:

| | |
|---|---|
| Gravity ° API/60° F. | 31 – 36.0 |
| Viscosity SUS/100° F. | 60 – 120 |
| Viscosity SUS/210° F. | 34 – 38 |
| Unsulfonated residue wt. percent | 75.0 – 99.9 |

* * * * *